United States Patent [19]
Avruch et al.

[11] Patent Number: 5,582,995
[45] Date of Patent: Dec. 10, 1996

[54] METHODS OF SCREENING FOR COMPOUNDS WHICH INHIBIT THE DIRECT BINDING OF RAS TO RAF

[75] Inventors: Joseph Avruch, Brookline; Xian-feng Zhang, Cambridge, both of Mass.

[73] Assignee: The General Hospital Corporation, Boston, Mass.

[21] Appl. No.: 77,256

[22] Filed: Jun. 11, 1993

[51] Int. Cl.⁶ .................... G01N 33/53; G01N 33/574
[52] U.S. Cl. .................... 435/71; 435/7.23; 435/69.1; 435/69.8; 435/69.9; 436/501; 436/64
[58] Field of Search .................... 435/7.1, 69.1, 435/69.8, 69.9, 7.23; 436/501, 64

[56] References Cited

FOREIGN PATENT DOCUMENTS

WO93/04170   4/1993   WIPO .

OTHER PUBLICATIONS

Fields et al. Nature 340 pp. 245–246 (1989) "A Novel Genetic System to Detect Protein—Protein Interactions".
Luban et al. J. Virol. 66 #8 pp. 5157–5160 (Aug. 1992) "Genetic Assay for Multimerization of Retroviral Gag Polyproteins".
Berg J. B. C. 265 #12 pp. 6513–6516 (1990) "Zinc Fingers and Other Metal–binding Domains".
Mulcahy et al. Nature 313 pp. 241–243 (1985) "Requirement for Gas Proto–Oncogene Function During Serum–Stimulated Growth of NIH NT3 Cells".
Rocquigny et al. Biochem. Biocphys. Res. Comm. 180 #2 pp. 1010–1016 (1991) "First Large Scale Chemical Synthesis of the 72 Amino Acid HIV–1 Nucleocapsid Protein NC p. 7 in an Active Form".
Zhang et al. Nature 364 pp. 308–313 (Jul. 1993) "Normal and Oncogenic p21[(a)] Proteins Bind to the Amino Terminal Regulatory Domain of c–Raf–1".
Dermer, Bio/Technology, vol. 12 Mar. 1994, p. 320 "Another Anniversary for the War on Cancer".
Plattner et al., "Obstacles to drug development from peptide leads", from *Drug Discovery Technologies*, Ed. by Clark et al., Ellis Harwodd Ltd. (1990), pp. 92–126.
TIG, vol. 10, #2, pp. 45–48 (1994) "The 3Rs of life: Ras, Raf and growth regulation".
Bonner et al.; The complete coding sequence of the human *raf* oncogene and the corresponding structure of the c–*raf*–1 gene; Nucleic Acids Research; 14: 1009–1015 (1986).
Bruder et al.; Serum–, TPA–, and Ras–induced expression from Ap–1/Ets–driven promoters requires Raf–1 kinase; Genes & Development; 6:545–556 (1992).
Chien et al.; The two–hybrid system: A method to identify and clone genes for proteins that interact with a protein of interest; Proc. Natl. Acad. Sci. USA; 88:9578–9582 (1991).
Durfee et al.; The retinoblastoma protein associates with the protein phosphatase type 1 catalytic subunit; Genes & Development; 7:555–569 (1993).
Guan et al.; Eukaryotic Proteins Expressed in *Escherichia coli*: An Improved Thrombin Cleavage and Purification Procedure of Fusion Proteins with Glutathione S–Transferase; Analytical Biochemistry; 192:262–267.

Heidecker et al.; The Role of Raf–1 Phosphorylation in Signal Transduction; Viral Pathology Section; Laboratory of Viral Carcinogenesis; NCI–Frederick Cancer Research and Development Center, Frederick, Maryland 21702.
Howe et al.; Activation of the MAP Kinase Pathway by the Protein Kinase raf; Cell; 71:335–342 (1992).
Huleihel et al.; Characterization of Murine A–*raf*, a New Oncogene Related to the v–*raf* Oncogene; Molecular and Cellular Biology; 6:2655–2662 (1986).
Itoh et al.; The Post–translational Processing of *ras*p21 Is Critical for Its Stimulation of Mitogen–activated Protein Kinase; The Journal of Biological Chemistry; 268:3025–3028 (1993).
Kitayama et al.; Genetic analysis of the Kirsten–*ras*–revertant 1 gene: Potentiation of its tumor suppressor activity by specific point mutations; Proc. Natl. Acad. Sci. USA; 87:4284–4288 (1990).
Kolch et al.; Raf–1 protein kinase is required for growth of induced NIH/3T3 cells; Nature; 349:426–428 (1991).
Kovacina et al.; Insulin Activates teh Kinase Activity of the Raf–1 Proto–oncogene by Increasing Its Serine Phosphorylation; The Journal of Biological Chemistry; 265:12115–12118 (1990).
Kyriakis et al.; Raf–1 activates MAP kinase—kinase; Nature; 358:417–421 (1992).
Marshall et al.; Characterization of Ras effector mutant interactions with the NF1–GAP related domain; Oncogene; 8:425–431 (1993).
Marshall et al.; Identification of Amino Acid Residues Required for Ras p21 Target Activation; Molecular and Cellular Biology; 11:3997–4004 (1991).
Mizuno et al.; A stimulatory GDP/GTP exchange protein for smg p21 is active on the post–translationally processed form of c–Ki–ras p21 and rhoA p21; Proc. Nat. Acad. Sci. USA; 88:6442–6446 (1991).
Quilliam et al.; Biochemical Characterization of Baculovirus–Expressed *rap*1A/Krev–1 and Its Regulation by GTPase–Activating Proteins; Molecular and Cellular Biology; 10:2901–2908 (1990).
Satoh et al.; Function of Ras as a Molecular Switch in Signal Transduction; The Journal of Biological Chemistry; 267:24149–24152 (1992).
Stanton et al.; Definition of the Human *raf* Amino–Terminal Regulatory Region by Deletion Mutagenesis; Molecular and Cellular Biology; 9:639–647 (1989).
Tsuda et al.; A Protein Kinase Similar to MAP Kinase Activator Acts Downstream of the Raf Kinase in Drosophila; Cell; 72:407–414 (1993).
Valencia et al.; The *ras* Protein Family: Evolutionary Tree and Role of Conserved Amino Acids; Biochemistry; 30:4637–4647 (1991).

*Primary Examiner*—Lora M. Green
*Attorney, Agent, or Firm*—Fish & Richardson P.C.

[57] ABSTRACT

Disclosed is a method of screening for compounds which inhibit the direct binding of Ras or Raf-binding fragments thereof to Raf or Ras binding fragments thereof.

2 Claims, No Drawings

5,582,995

METHODS OF SCREENING FOR COMPOUNDS WHICH INHIBIT THE DIRECT BINDING OF RAS TO RAF

STATEMENT AS TO FEDERALLY SPONSORED RESEARCH

This invention was made with Government support under DK41513 and DK41762 awarded by the National Institutes of Diabetes and Digestive and Kidney Diseases. The Government has certain rights in the invention.

BACKGROUND OF THE INVENTION

The invention relates to signal transduction.

The ras gene was discovered as an oncogene of the Harvey (rasH) and Kirsten (rasK) rat sarcoma viruses. In humans, characteristic mutations in the cellular ras gene (c-ras) have been associated with many different types of cancers. These mutant alleles, which render Ras constitutively active, have been shown to transform cells, such as the murine cell line NIH 3T3, in culture.

The ras gene product binds to guanine triphosphate (GTP) and guanine diphosphate (GDP) and hydrolyzes GTP to GDP. It is the GTP-bound state of Ras that is active. An accessory molecule, GTPase-activating protein (GAP) also binds to Ras and accelerates the hydrolysis of GTP. The ras proto-oncogene requires a functionally intact raf-1 proto-oncogene in order to transduce growth and differentiation signals initiated by receptor and non-receptor tyrosine kinases in higher eukaryotes. Activated Ras is necessary for the activation of the c-raf-1 proto-oncogene, but the biochemical steps through which Ras activates the Raf-1 protein (Ser/Thr) kinase are not well characterized.

SUMMARY OF THE INVENTION

It has been discovered that zinc-finger domain containing proteins can interact directly with other proteins. Although not being bound by theory, it is believed that the interaction occurs via the zinc-finger domain. (Zinc-finger domains were previously thought to be active primarily in interactions between zinc-finger domain containing proteins and nucleic acids.) For example, a direct interaction between Ras and the regulatory zinc-finger containing domain of Raf has been discovered.

Accordingly, the invention features a method of evaluating a compound, e.g., for the ability to bind to zinc-finger domains, for signal-transduction-inhibiting properties, for cell proliferation inhibiting properties, for the ability to alter the cell cycle, or for the ability to inhibit a biological activity, e.g., the ability to bind to another protein, e.g., an oncogene protein or an oncogene protein substrate, of a zinc-finger domain containing protein, an oncogene protein, a cellular oncogene protein, or a proto-oncogene protein. The method includes contacting the compound with a zinc-finger domain containing protein e.g., a signal transduction protein, e.g., an oncogene protein, e.g., Raf, a Ras-binding fragment of Raf, e.g., Raf residues 1–257 [Raf(1–257)] [MEHIQGAWKTISNGFGFKDAVFDGSS-CISPTIVQQFGYQRRASDDGKLTDPSKTSNTIR VFLP-NKQRTVVNVRNGMSLHDCLMKALKVR-GLQPECCAVFRLLHEHKGKKARLDWNTDAA SLIGEELQVDFLDHVPLTTHNFARKT-FLKLAFCDICQKFLLNGFRCQTCGYKFHEHCSTK VPTMCVDWSNIRQLLLFNPSTIGDS-GVPQLPSLTMRRRMRESVSRMPRYSTPHAFTFNTSS PSSEGSLSQRQRS (SEQ ID NO:1)] or Raf residues 152–168 [Raf(152–168)] [CDICQKFLLNGFRCQTC (SEQ ID NO:2)], a proto-oncogene or a cellular oncogene protein; and determining the ability of the compound to bind to the protein. The binding affinity of the compound for the protein is correlated to one or more of the above mentioned properties. In preferred embodiments, binding can be determined by elution with a second protein known to bind the zinc-finger domain containing protein, e.g., Ras or a Raf-binding fragment of Ras can be used to elute a compound bound to Raf. Other methods can also be used to elute the candidate compound such as the use of antibodies which bind to the protein and thus can disrupt the protein/compound interaction; ionic or non-ionic detergent; chaotropic agents; or altered pH or salt concentration.

In another aspect, the invention features a method of evaluating a compound, e.g., for signal-transduction-inhibiting properties, for cell proliferation inhibiting properties, for the ability to alter the cell cycle, or for the ability to inhibit the biological activity, e.g., the ability to bind to another protein, e.g., an oncogene protein or an oncogene protein substrate, of a zinc-finger domain containing protein, an oncogene protein, cellular oncogene protein or proto-oncogene protein. The method includes contacting the compound with a protein e.g., a signal transduction protein, e.g., an oncogene protein, e.g., Ras, or a Raf-binding fragment of Ras, e.g., Ras residues 1–186 [Ras(1–186)] [MTEYKLV-VVGAGGVGKSALTIQLLIQNHFVDEYDP-TIEDSYRKQVVIDGETCLLDILDT AGQEEYSAM-RDQYMRTGEGFLCVFAINNTKSFEDIHQYREQIKRV-KDSDDVPMVLVGNKC DLAARTVESRQAQDLARSYGIPYIET-SAKTRQGVEDAFYTLVREIRQHKLRKLNPPDESG PQCMSCKC (SEQ ID NO:3)] or Ras residues 32–40 [Ras(32–40)] [YDPTIEDSY (SEQ ID NO:4)], a proto-oncogene or a cellular oncogene protein; and determining the ability of the compound to bind the signal transduction protein. The binding affinity of the compound for the signal transduction protein is correlated to one or more of the above mentioned properties. In preferred embodiments, binding can be determined by elution with a protein known to bind to the signal transduction protein, e.g. Raf, or a Ras-binding fragment of Raf can be used to elute a compound bound to Ras. Other methods can also be used to elute the candidate compound such as the use of antibodies which bind to the signal transduction protein; ionic or non-ionic detergent; chaotropic agents; or altered pH or salt concentration.

The invention features a method of evaluating a compound for the ability to mimic the ability of the Rap protein to inhibit Raf activation or cell proliferation. The method includes contacting the compound with Raf or a Rap-binding fragment of Raf, e.g., Raf residues 1–257 or Raf residues 152–168, a proto-oncogene protein or a cellular oncogene protein; and determining the ability of the compound to bind to Raf or a fragment thereof. The binding affinity of the compound for Raf or a Rap-binding fragment of Raf is correlated to the above mentioned property. In preferred embodiments, binding can be determined by elution with Rap or a Raf-binding fragment of Rap to elute a compound bound to Raf. Other methods can also be used to elute the candidate compound such as the use of antibodies which bind to Raf; ionic or non-ionic detergent; chaotropic agents; or altered pH or salt concentration.

The screening method described in the previous paragraph can be used to identify candidate compounds with anti-oncogene or tumor suppressor activity. Rap binds to but does not activate wild type Raf, thus it acts as an antagonist of Ras activity. Identification of compounds which bind to Rap-binding sequences of Raf would be likely to mimic the activity of Rap polypeptides, which are identical to Ras in the effector domain (amino acid residues 32–40), have been shown to inhibit the Ras signal transduction pathway and suppress the transformed phenotype in cultured cells.

In another aspect, the invention features a method of evaluating a compound, e.g., for the ability to bind to zinc-finger domains, for signal-transduction-inhibiting properties, for cell proliferation inhibiting properties, for the ability to alter the cell cycle, or for the ability to inhibit the biological activity, e.g., the ability to bind to another protein, e.g., an oncogene protein or an oncogene protein substrate, of a zinc-finger domain containing protein, an oncogene protein, cellular oncogene protein or proto-oncogene protein. The method includes contacting the compound with a zinc-finger domain containing protein and a preselected protein and determining the ability of the compound to interfere with the binding of the preselected protein with the zinc-finger domain containing protein. The ability to interfere with the binding is correlated to the compound's ability to interfere with the zinc-finger domain-containing protein's interaction with the preselected protein and thus to affect one of the properties described above.

In preferred embodiments: the zinc-finger domain containing protein is a first signal transduction protein, e.g., an oncogene protein, e.g., Raf, a proto-oncogene or a cellular oncogene protein; the preselected protein is a protein the biological activity of which is altered, e.g., activated, by the zinc-finger domain containing protein; the preselected protein is a second signal transduction protein, e.g., an oncogene protein, e.g., Ras, a proto-oncogene or a cellular oncogene protein; the preselected protein is a substrate which is phosphorylated or dephosphorylated by the zinc finger-domain containing protein; the first signal transduction protein is Ras or a Raf-binding fragment of Ras, e.g., Ras residues 1–186 or Ras residues 32–40 and the preselected protein is Raf or a Ras-binding fragment of Raf, e.g., Raf residues 1–257 or Raf residues 152–168.

In another aspect, the invention features a method of evaluating the cell proliferation inhibiting properties of a compound. The method includes: contacting the compound with Raf or a Ras-binding fragment of Raf, e.g., Raf residues 1–257 or Raf residues 152–168; contacting the compound with Ras or a Raf-binding fragment of Ras, e.g., Ras residues 1–186 or Ras residues 32–40; and determining the ability of the compound to interfere with the binding of Ras or a Raf-binding fragment of Ras to Raf or a Ras-binding fragment of Raf. The ability to interfere with binding is correlated to the cell proliferation inhibiting properties of the compound.

In another aspect, the invention features a method of screening a candidate compound for the ability to inhibit an interaction of a zinc-finger domain containing protein with a preselected protein. The method includes: (a) providing GAL4 binding site linked to a reporter gene, e.g., the lacZ gene; (b) providing a GAL4 binding domain linked to the zinc-finger domain containing protein or to a biologically active fragment thereof (wherein biologically active means capable of binding to the preselected protein); (c) providing a GAL4 transactivation domain II linked to the preselected protein or a biologically active fragment thereof (wherein biologically active means capable of binding to a zinc-finger containing protein); (d) administering the candidate compound; and (e) monitoring expression of the reporter gene, wherein a decrease in expression is an indication that the candidate compound inhibits an interaction of the zinc-finger domain containing protein and the preselected protein.

In the example above, the zinc-finger domain containing protein is coupled to the GAL4 binding domain and the preselected protein to the GAL4 transactivation domain II. The screening assay of the invention also allows for coupling of the zinc-finger domain containing protein to the GAL4 transactivation domain II and the preselected protein to the GAL4 binding domain.

In preferred embodiments: the zinc-finger domain containing protein is a first signal transduction protein, e.g., an oncogene protein, e.g., Raf, a proto-oncogene protein or a cellular oncogene protein; the preselected protein is a protein the biological activity of which is altered by the zinc-finger domain containing protein; the preselected protein is a second signal transduction protein, e.g., an oncogene protein, e.g., Ras, a proto-oncogene protein or a cellular oncogene protein; the preselected protein is a substrate which is phosphorylated or dephosphorylated by the zinc finger-domain containing protein; the first signal transduction protein is Ras or a Raf-binding fragment of Ras.

In another aspect, the invention features, a method of inhibiting unwanted cell proliferation in an animal, e.g., a mammal, e.g., a human. The method includes administering an effective amount of Ras or a Raf-binding fragment of Ras to the animal, wherein the polypeptide inhibits an interaction of Ras with Raf.

In preferred embodiments, the fragment is a polypeptide consisting essentially of the amino acid sequence of Ras(1–186); the fragment is a polypeptide consisting essentially of the amino acid sequence of Ras(32–40).

In another aspect, the invention features, a method of inhibiting unwanted cell proliferation in an animal, e.g., a mammal, e.g., a human. The method includes administering an effective amount of Raf or a Ras-binding fragment of Raf to the animal, wherein the polypeptide inhibits an interaction of Ras with Raf.

In preferred embodiments, the fragment is a polypeptide consisting essentially of the amino acid sequence of Raf(1–257); the fragment is a polypeptide consisting essentially of the amino acid sequence of Raf(152–168).

In another aspect, the invention features a preparation of antibodies, preferably a monoclonal preparation which consists essentially of antibodies which specifically bind to a polypeptide consisting of Ras(32–40). In preferred embodiments, the preparation is free of antibodies which bind to epitopes outside the region of Ras residues 32–40. The invention includes a method of inhibiting unwanted cell proliferation in an animal, e.g., a mammal, e.g., a human, by administering a preparation of antibodies of the invention.

In another aspect, the invention features an antibody preparation, preferably a monoclonal antibody preparation which specifically binds to a complex comprising Ras bound to Raf, wherein the antibody does not bind to Ras or Raf alone. The invention includes a method of inhibiting unwanted cell proliferation in an animal, e.g., a mammal, e.g., a human, by administering an antibody, e.g., a monoclonal antibody which binds to the Ras/Raf complex.

In another aspect, the invention features a method of purifying a compound, e.g., an anti-proliferative compound which inhibits the binding of a zinc finger-domain containing protein, e.g., a signal transduction protein, e.g., an oncogene protein, a proto-oncogene protein or a cellular oncogene protein with second protein, e.g., the interaction of Raf or a Ras-binding fragment of Raf with Ras, and isolating said compound by its binding affinity for the zinc finger-domain containing protein. In preferred embodiments, the second protein is a signal transduction protein, e.g., an oncogene protein, e.g., Ras, a proto-oncogene or a cellular oncogene protein; the preselected protein is a substrate which is phosphorylated or dephosphorylated by the zinc finger-domain containing protein; the first signal transduction protein is Ras or a Raf-binding fragment of Ras, e.g., Ras residues 1–186 or Ras residues 32–40 and the preselected protein is Raf or a Ras-binding fragment of Raf, e.g., Raf residues 1–257 or Raf residues 152–168.

In another aspect, the invention features a method of purifying an anti-proliferative compound. The method includes contacting the compound with Ras or a Raf-binding fragment of Ras, e.g., Ras residues 1–186 or Ras residues 32–40 and isolating the compound by its binding affinity for Ras or the Raf-binding fragment of Ras.

The invention includes purified preparations of the proteins, peptides, and antibodies of the invention. Purified preparations, used herein, refers to the preparations which are at least 5%, by dry weight the protein, peptide or antibody of the invention.

The term zinc finger domain as used herein refers to a metal coordinating structure formed by two and preferably three cysteine residues spaced apart so as to coordinate a zinc atom, e.g., the structure formed by the amino acid sequence, CXXCXXXXXXXXXCXXC (SEQ ID NO:5).

The peptides, proteins and antibodies of the invention can be used to alter receptor and non-receptor mediated signal transduction and inhibit the aberrant proliferation of cells. The screening methods of the invention are simple, rapid and efficient assays designed to identify compounds with anti-proliferative and tumor suppressor activity. Peptides and antibodies of the invention as well as compounds identified using the screening methods of the invention can be used to treat animals, including human patients, afflicted with disease states characterized by disregulated signal transduction or aberrant cell proliferation, such as tumors and autoimmune diseases.

Other features and advantages of the invention will be apparent from the following detailed description and from the claims.

DETAILED DESCRIPTION

Construction of GST fusion proteins

To facilitate the expression, purification, and solid state immobilization of polypeptides such as Ras or Raf, GST fusion proteins can be made. A chimeric gene encoding a GST fusion protein can be constructed by fusing DNA encoding a polypeptide or polypeptide fragment to the DNA encoding the carboxyl terminus of GST (see e.g., Smith et al., 1988, Gene 67:31). The fusion construct, can be transformed into a suitable expression system, e.g., E. coli XA90 in which the expression of the GST fusion protein can be induced with isopropyl-β-D-thiogalactopyranoside (IPTG).

Purification of GST fusion proteins

After transformation of the resulting construct into a suitable expression system, induction with IPTG should yield the fusion protein as a major constituent of soluble, cellular proteins. The fusion proteins can be purified by methods known to those skilled in the art, including purification by glutathione affinity chromatography. The purity of the product can be assayed by methods known to those skilled in the art, e.g., gel electrophoresis.

Binding of Ras to immobilized GST-Raf

GST fusion proteins can be complexed to glutathione which is attached to a matrix material, e.g., glutathione Sepharose, by methods known to those skilled in the art.

Ras-binding fragments of Raf; Raf-binding fragments of Ras

Fragments of Ras which bind Raf (or fragments of Raf which bind Ras) can be made by methods known to those skilled in the art. For example, a DNA fragment which expresses a putative Raf-binding Ras fragment can be fused to GST (as described herein), the fusion protein immobilized by binding to glutathione-Sepharose, and the ability of the fusion protein to bind Raf or a fragment thereof determined.

In vitro direct binding of Raf to Ras

Wild type Ras and Rash in which the valine at position 12 has been replaced with glycine (V12GrasH) bind specifically to the aminoterminal regulatory segment of Raf-1 in a GTP dependent fashion. The binding of Ras to Raf(1–257) is strongly dependent on the nature of the guanyl nucleotide bound to Ras. The V12GrasH, charged to a similar extent with either GTPγS or GDPβS, was incubated with the GST-Raf fusion proteins. Significantly less GDPβS-Ras polypeptide was retained by Raf(1–257) as compared to incubations containing identical concentrations of Ras polypeptide in the GTPγS-bound form. Thus the GTP-charged, active form of Ras exhibits a substantially higher apparent affinity for Raf(1–257).

These experiments were performed as follows. The raf-1 gene product has an ATP-binding site, a carboxyterminal catalytic domain and aminoterminal regulatory domains termed CR1 and CR2. Glutathione-S-transferase (GST) fusion proteins were made by cloning DNA sequences encoding an aminoterminal fragment of c-raf-1 comprising the first 257 amino acid residues [Raf(1–257)], and a mutant fragment in which a serine residue replaces a cysteine residue at position 168 [Raf (1–257, $C_{168}$→S)]. GST alone was used as a control. Fusion proteins and GST were added at equal concentrations to varying amounts of GTPγS-loaded-V12GrasH. V12GrasH bound to GST-Raf(1–257) in a dose-dependent manner compared to the absence of detectable binding of GTPγS-V12GrasH to GST alone. GTPγS-V12GrasH also binds to the mutant GST-Raf(1–257 $C_{168}$→S), however at any concentration of Ras tested, significantly lower amounts of Ras are retained by equal amounts of the mutant Raf(1–257, $C_{168}$→S) as compared to the wild-type Raf(1–257).

Incompletely processed Bas protein can bind the Raf aminoterminal domain

Ras undergoes a series of sequential posttranslational modifications at its carboxyterminus, consisting of S-farnesylation at $C_{186}$, proteolytic cleavage after $C_{186}$, carboxymethylation of the $C_{186}$ carboxyterminus, and palmitoylation at one or more cysteines upstream (Hancock, J. F. et al. Cell 57, 1167–1177 (1989)). When expressed in Spodoptera frugiperda (Sf9) cells, approximately 10% of the rasH polypeptide is associated with the membrane fractions, and a substantial portion of this has been shown to be palmitoylated, indicating that the Ras polypeptide has been fully processed. The cytoplasmic forms of baculoviral rash are not palmitoylated, although some molecules may be farnesylated (Page, M. J. et al. J. Biol. Chem. 264, 19147–19156 (1989). The ability of membrane derived and cytoplasmic recombinant V12GrasH polypeptides from Sf9 cells in their ability to bind to GST-Raf(1–257) was compared. The Ras polypeptides were each purified and charged with $^{35}$S-GTPγS to a stoichiometry of approximately 1.0. At approximately equal concentrations, and under similar conditions, both the cytoplasmic and membrane-derived forms of Ras bound effectively to GST-Raf(1–257) in preference to the mutant GST-Raf(1–257, $C_{168} \rightarrow S$). These data indicate that a fully processed Ras polypeptide is not essential for the binding of Ras to the Raf aminoterminal domain.

In vitro direct binding experiments were carried out as follows. GST, GST-Raf(1 to 257) and GST-Raf(1–257, $C_{168} \rightarrow S$), immobilized on glutathione-agarose beads, were incubated with GTPγS-loaded, baculoviral recombinant, cytosolic V12GrasH or an equal amount of the same Ras polypeptide loaded with GDPβS; parallel experiments lacked added Ras After 6 hours of tumbling at 4° C., the glutathione agarose beads were washed and analyzed for the binding of Ras polypeptide by sodium dodecyl sulfate-polyacrylamide gel electrophoresis (SDS-PAGE), followed by immunoblotting using a pan-Ras monoclonal antibody-2 (Oncogene Science).

Baculoviral recombinant V12GrasH, partially purified from either the membrane pellet or cytosol, were brought to approximately the same concentration of Ras polypeptide, loaded in parallel with GTPγS, and incubated with GST-Insulin-receptor-substrate-1 (IRS-1) as a control fusion protein, GST-Raf(1–257), or GST-Raf(1–257, $C_{168} \rightarrow S$) immobilized on glutathione agarose. After 6 hours tumbling at 4° C., the beads were washed and analyzed for the binding of Ras polypeptide.

Recombinant Ras polypeptides

For production of recombinant Ras polypeptide, Sf9 cells grown in monolayer, were infected at 5× multiplicity of infection (MOI) with a recombinant baculovirus encoding V12GrasH. Sixty five to 72 hours post infection, cells were harvested as in (Mizuno, T. et al. *Proc. Natl. Acad. Sci. U.S.A.* 88, 6442–6446 (1991)), sonicated, and centrifuged at 100,000×g for 1 hour. The Ras polypeptides in the membrane pellet and cytosol were each purified separately using Mono Q anion exchange chromatography, as in (Mizuno, T. et al. *Proc. Natl. Acad. Sci. U.S.A.* 88, 6442–6446 (1991)) employing 30 mM n-octylglucoside in both purifications. The peak of $^{35}$S-GTPγS binding corresponded to the Ras polypeptide detected by immunoblotting. Both preparations, (stored at –80 in 20 mM TrisCl, pH8, 5 mM MgCl$_2$, 1 mM EDTA, 1 mM DTT, 30 mM n-octylglucoside, ~0.25M NaCl) were approximately 10% pure.

Nucleotide loading of Ras was carried out by dilution to the desired polypeptide concentration, and addition to an equal volume of 2× loading buffer (0.1M TrisCl pH 7.5, 15 mM EDTA, 1 mg/ml BSA, 2 mM DTT, 1 mM GTPγS or GDPβS). After 15 min. at 37° C., MgCl$_2$ was added to a final concentration of 12.5 mM, and the Ras polypeptide was placed on ice. Charging of Ras with $^{35}$S-labeled guanyl nucleotides under these conditions resulted in a stoichiometry near 1.0 for both GTPγS and GDPβS. A mock GTP/GDP charging reaction contained all components except that Ras was replaced by Ras storage buffer.

Recombinant GST-Raf fusion proteins

The DNA sequences encoding Raf-1 amino acid residues 1–257 were generated by the polymerase chain reaction (PCR), using as template the plasmids RSV-C4 and RSV-PM17 (Bruder, J. T., Heidecker, G. & Rapp, U. R. *Genes Dev.* 6, 545–556 (1992)), which encode the wild-type and $C_{168} \rightarrow S$ mutant sequences, respectively. The c-DNA were inserted into pGEX-KG (Guan, K. L. and Dixon J. E., *Anal Biochem.* 192, 262–267 (1991)) at the EcoR1 and Sal1 sites, and sequenced to confirm the mutation and proper in-frame insertion. The GST-Raf fusion proteins, and the GST polypeptide were purified on glutathione agarose, and eluted with glutathione (12.5 mM) in 50 mM TrisCl pH 7.5, 0.15M NaCl, 1 mM DTT, 1.0% Triton-X-100 (Buffer A). Glutathione was removed from the eluted fusion protein by dialysis against buffer A. The GST-Raf(1–257) and GST-Raf(1–257, $C_{168} \rightarrow S$) were indistinguishable on a stained polyacrylamide gel. About 50% of the recombinant polypeptides were recovered as full-length fusion proteins. The purified GST and GST-Raf fusion proteins were each incubated with glutathione agarose at a concentration of 7 mg polypeptide/ml settled beads with tumbling at 4° C. for 30 min. The beads were washed 4× and resuspended in buffer A as a 50% suspension. 50 µl of the glutathione agarose suspensions were mixed with 80 µl of GTPγS charged cytosolic Ras, 80 µl of mock GTP charging reaction, or 20 µl of GTP-charged Ras plus 60 µl of mock GTP charging reaction. In parallel, 80 µl of GDPβS charged Ras, 80 µl of mock GDP charging reaction, or 20 µl of GDPβS charged Ras plus 60 µl of mock GDP charging reaction were added to 50 µl of the glutathione agarose bead suspensions. Buffer A (0.6 ml), containing a final concentration of 0.2% BSA, 5 mM MgCl$_2$, 25 mM ZnCl$_2$ pH 7.5, was added to all tubes. The suspension was tumbled at 4° C. for 6 hours, washed 5× in buffer A, eluted into sodium dodecyl sulfate (SDS), subjected to SDS-PAGE. Following transfer to polyvinylidene difluoride (PVDF) membrane, the membrane was immunoblotted using pan-Ras monoclonal antibody-2 (Oncogene Science) and detected using the enhanced chemi-luminescence technique (Amersham).

The membrane-derived and cytosolic Ras preparations were diluted to approximately the same Ras polypeptide concentration, as assayed by immunoblot and gel staining, charged with GTPγS in parallel, and incubated with immobilized GST fusion proteins as described above. A GST-IRS-1 fusion protein was employed as control in place of GST. The Ras standard polypeptide was purchased from Oncogene Science.

Raf (1–257) inhibition of c-rasH GTPase activity

Raf(1–257) inhibits the Ras-GAP stimulation of c-rasH GTPase. The intrinsic rate of Ras-catalyzed hydrolysis of $\gamma^{32}$P-GTP is not altered by recombinant GST-Raf(1–257). In contrast, the ability of p120 Ras-GAP to stimulate Ras GTPase can be potently inhibited by GST-Raf(1–257) added at a concentration nearly equal to Ras-GAP, whereas GST alone has no effect. The mutant GST-Raf(1–257, $C_{168} \rightarrow S$), at identical concentration, gives significantly less inhibition of Ras-GAP than the wild-type GST-Raf(1–257) polypeptide.

The ability of recombinant GST, GST-Raf(1–257) and GST-Raf(1–257, $C_{168} \rightarrow S$) to alter c-rasH GTPase activity was determined in the absence and presence of Ras-GAP. The GTPase activity was estimated from the $\gamma^{32}$P-GTP remaining bound to c-rasH after filtration.

In these experiments, baculoviral recombinant c-rasH was expressed and purified from the membrane pellet of Sf9 cells as described for the baculoviral membrane V12GrasH above. The c-rasH was charged with $\gamma^{32}$P-GTP by combining 0.1 ml of c-rasH (approximately 10 µg/ml) in Ras storage buffer with 0.3 ml of 60 mM TrisCl, pH 7.5, 5 mM EDTA, 0.7 mg/ml BSA, 1.5 mM DTT, 4 mM ATP, 0.142 µM $\gamma^{32}$P-GTP (4–6×10$^5$ cpm/pmole) on ice. After 1 hour, 50 µl of 135 mM MgCl$_2$ was added. Loading of c-rasH with $\alpha^{32}$P-GTP was carried out under the same conditions; the $\alpha^{32}$P-GTP-c-rasH was separated from unbound nucleotide by gel filtration (PD-10) in 25 mM TrisCl, pH 7.5, 5 mM MgCl$_2$, 3 mM ATP, 1 mM DTT, and stored on ice. Baculoviral recombinant, full-length human GAP protein was extracted from Sf9 cells by homogenization in 25 mM TrisCl pH 7.5, 1 mM EGTA, 5 mM MgCl$_2$, 1 mM DTT (GAP buffer) and protease inhibitors. The clarified supernatant was subjected to anion exchange chromatography on FastQ Sepharose equilibrated with GAP buffer and eluted with NaCl in a gradient to 0.4M. GAP was detected using a radiolabeled Ras polypeptide in a filter binding assay. The peak containing Ras-GAP was precipitated at 50% (NH$_4$)$_2$SO$_4$, dialyzed against a modified GAP buffer wherein 25 mM 2-[N-morpholino]ethanesulfonic acid (MES) pH 6.5 replaced Tris, and subjected to MonoS cation exchange chromatography in MES-GAP buffer. Peak fractions were pooled and dialyzed against MES-GAP buffer containing 20% glycerol. 4 μl of GAP (0.03 μg/ml) or MES-GAP buffer were combined with 4 μl of GST, GST-Raf(1–257) or GST-Raf(1–257, C$_{168}$→S) (each at 0.1 mg/ml in buffer A). The reaction was started by addition of 20 μl of $\gamma^{32}$P-GTP loaded c-rasH. After 15 min at 30° C., 1 ml of a stop solution containing 25 mM TrisCl pH 8, 0.1M NaCl, 30 mM MgCl$_2$, 2 mM DTT, and 1 mg/ml BSA was added. The mixture was filtered through a BA85 nitrocellulose membrane, washed 3× with 4 ml of stop solution, and the filters analyzed for retained $^{32}$P-labeled nucleotide. The identity of the a $^{32}$P-labeled nucleotide was analyzed by TLC on polyethyleneimine (PEI) cellulose plates developed in 0.75M KPO$_4$, pH 3.65.

In situ binding of Raf to Ras in a two-hybrid yeast expression system

Protein-protein interactions can be identified in vivo using a two-hybrid expression system wherein the activity of a transcriptional activator is reconstituted.

The yeast GAL4 protein consists of functionally distinguishable domains. One domain is responsible for DNA-binding and the other for transcriptional activation. In the two-hybrid expression system, plasmids encoding two hybrid proteins, one containing the GAL4 DNA-binding domain fused to protein a first protein and the other containing the GAL4 activation domain fused to a second protein are introduced into yeast. If the two proteins are able to interact with one another, the ability to activate transcription from promoters containing Gal4-binding sites, upstream activating sequence from GAL1 (UAS$_G$) is reconstituted leading to the expression of a reporter gene.

Protein-protein interactions of multiple Ras variants were detected through the ability of such interactions to reconstitute the transactivating function of the GAL4 protein in a yeast expression system (Durfee, T. et al. *Genes Develop.* 7, 555–569 (1993)). The cDNA sequences encoding c-Raf(1–257) and the c-Raf(1–257, C$_{168}$→S) mutant were inserted into the pMA424 plasmid (Chien C. T., Bartel P. L., Sternglanz, R., Fields, S., *Proc. Natl. Acad. Sci. U.S.A.* 88, 9578–9582 (1991)), fused in-frame to DNA sequences encoding GAL4 amino acid residues 1–147 (GAL4 DNA binding domain).

pACT is a vector that encodes DNA sequences corresponding to amino acids 768–881 (GAL4 transactivation domain II) (Kitayama, H., Matsuzaki, T., Ikawa, Y. & & Noda, M. *Cell* 56, 77–84 (1989)). Coexpression of pMA424 Raf(1–257) or pMA424 Raf(1–257, C$_{168}$→S) with pACT in a yeast strain that contains a GAL4 binding site (from the upstream activating sequence of Gal1) driving expression of a lacZ reporter gene, did not provide any activation of lacZ expression. Fusion of DNA sequences encoding a V12GrasH polypeptide in-frame with the GAL4 transactivating domain in pACT led to the appearance of several colonies exhibiting strong lacZ expression in the cotransfection with wild-type Raf(1–257) sequences, but not mutant Raf(1–257, C$_{168}$→S).

A decrease in transformation efficiency was observed on expression of the ras sequences, whether transfected with either the wild-type or mutant Raf-1 aminoterminus. Since a fully processed Ras carboxyterminus did not appear critical to the interaction in vitro between Raf(1–257) and Ras described earlier, the V12GrasH DNA sequences in pACT were modified so as to remove the carboxyterminal four amino acid residues (ΔCT). This truncation completely eliminated the growth inhibitory effect of the pACT encoded ras sequences. Under these conditions, it is evident that the expression of V12GrasHΔCT together with wild-type Raf(1–257) strongly reconstitutes the GAL4-driven expression of lacZ, whereas coexpression of V12GrasH ΔCT with the mutant Raf(1–257, C$_{168}$→S) results in very weak expression of lacZ. A similar pattern of lacZ expression was obtained if the Raf(1–257) DNA sequences in pMA424 were exchanged into pACTII, and cotransformed with pMA424 containing the ras or rap 1b inserts.

The Rap 1a (Pizon, V. et al. *Oncogene* 3, 201–204 (1988)) and 1b (Pizon, V., Lerosey, L., Chardin, P. & Tavitian, A. *Nucleic Acids Res.* 16, 7719 (1988)) polypeptides (identical to each other over residues 4–106) are low molecular weight GTP binding proteins identical to Ras in the effector domain (amino acid residues 32–40). Rap-1a (Krev-1) was identified as a suppressor of the transformed phenotype induced by v-rasK in NIH 3T3 cells (Kitayama, H., Matsuzaki, T., Ikawa, Y. & & Noda, M. *Cell* 56, 77–84 (1989)); Rap 1a itself is nontransforming. Rap 1b has been shown to antagonize the action of Ras in *Xenopus oocytes* (Campa, M. J. et al. *Biochem. Biophys. Res. Comm.* 174, 1–5 (1991)). Mutation within the Rap-1 effector domain impairs its ability to act as an inhibitor of Ras transformation (Kitayama, H., Mtsuzaki, T., Ikawa, Y. & Noda, M. *Proc. Natl. Acad. Sci. U.S.A.* 87, 4284–4288 (1990)). These observations suggest that the identical effector domain in Rap-1a/1b and Ras may permit binding to a common Ras effector, and in fact Rap-1a binds Ras-GAP with high affinity (Hata, P. et al. *J. biol. Chem.* 265, 7104–7110 (1990); Frech, M. et al. *Science* 249, 169–171 (1990)); clearly, however, Ras residues 32–40 in the Rap-1a context fails to activate and actually inhibits the Ras signal transduction pathway. In view of these properties, it is noteworthy that V12Grap-1b and the V12Grap-1bΔCT interact strongly with Raf(1–257) to activate lacZ expression, while exhibiting no detectable interaction with the mutant Raf(1–257, C$_{168}$→S).

The preferential binding of Ras to the wild-type Raf aminoterminal sequences over mutant Raf confirms the results seen with direct binding experiments in vitro. The ability of wild-type Raf(1–257) and mutant Raf(1–257 C$_{168}$→S) to interact with a series of V12GrasHΔCT structures containing mutations in and around the Ras effector domain was evaluated by reconstituting GAL4-dependent lacZ expression in yeast (Table 1).

The Ras effector domain has been identified as a region essential for transformation and Ras binding to p120 Ras-GAP. Mutations in this region have been shown not to alter the biochemical activities intrinsic to Ras, i.e. nucleotide binding and hydrolysis and membrane localization. Two V12GrasHΔCT constructs containing mutations within the effector domain [D$_{38}$→N, deletion of P34 (Δ34), D$_{38}$→A] known to abrogate Ras binding to GAP as well as Ras transforming activity in NIH 3T3 cells (Table 1) (Marshall, M. S. et al. *Molec. Cell Biol.* 11, 3999–4004 (1991); Marshall, M. S. & Hettich, C. A. *Oncogene* 8, 425–431

(1993)), were examined for interaction with Raf(1–257); both effector mutants failed completely to activate lacZ expression on cotransfection with either the wild-type or mutant raf-1 sequences (Table 1).

Mutation of Ras residues 26, 27, 30, 31 and 45, adjacent to the Ras effector domain, have been shown to impair Ras transforming activity despite modest or no impairment in Ras affinity for Ras-GAP (34). The effects of mutations at these residues, inserted into the V12GrasHΔCT sequence, on activation of lacZ expression in collaboration with Raf(1–257) is shown in Table 1. The $D_{45} \rightarrow E$ mutation is known to greatly impair Ras transforming activity, despite enhanced binding of this mutant Ras to Ras-GAP and neurofibromatosis-type 1 gene product (NF1), and a normal sensitivity to GAP stimulation of Ras GTPase (Marshall, M. S. & Hettich, C. A. *Oncogene* 8, 425–431 (1993)). The $D_{45} \rightarrow E$ mutation inserted into V12GrasHΔCT construct markedly reduced the ability of V12GrasHΔCT to activate lacZ expression in collaboration with Raf(1–257). The alteration of Ras residues $N_{26}H_{27} \rightarrow G$ and I, respectively, also spares GAP binding and responsiveness while decreasing substantially Ras transforming activity (although somewhat less severely than $D_{45} \rightarrow E$)(Table I) (Marshall, M. S. et al. *Molec. Cell Biol.* 11, 3999–4004 (1991); Marshall, M. S. & Hettich, C. A. *Oncogene* 8, 425–431 (1993)). Insertion of the $G_{26}I_{27}$ mutation into V12GrasHΔCT diminished substantially the activation of lacZ expression on coexpression with Raf(1–257), although to a lesser degree than $D_{45} \rightarrow E$ (Table 1). Alteration of Ras residues $D_{30}E_{31} \rightarrow E$ and K, respectively, reduces Ras binding to GAP and Ras transforming ability in a proportionate manner by 80–90% (Table 1) (Marshall, M. S. et al. *Molec. Cell Biol.* 11, 3999–4004 (1991); Marshall, M. S. & Hettich, C. A. *Oncogene* 8, 425–431 (1993)). The $E_{30}K_{31}$ V12GrasHΔCT structure exhibits a modestly impaired ability to stimulate lacZ expression in collaboration with Raf(1–257).

Detection of protein-protein interactions using the two-hybrid system in yeast was carried out as follows. The vector pMA424 (Chien C. T., Bartel P. L., Sternglanz, R., Fields, S., *Proc. Natl. Acad. Sci. U.S.A.* 88, 9578–9582 (1991)) containing either Raf(1–257) or Raf(1–257, $C_{168} \rightarrow S$) DNA sequences fused in frame with the sequences encoding GAL4 (1–147), was cotransformed into yeast together with the pACTII vector containing no insert as a control, or DNA sequences encoding V12GrasH, V12GrasHΔCT, murine rap1b, or rap1bΔCT fused in frame with the GAL4 transactivation domain II. After 3 days growth on selective media, the colonies were replica-plated to selective media, containing 5-bromo-4-chloro-3-indolyl-β-D-galactopyranoside (X-gal) and photographed 3 days later.

The DNA sequences encoding Raf(1–257) and Raf(1–257, $C_{168} \rightarrow S$) were prepared by the PCR using the plasmids RSV-C4 and RSV-PM17 (Bruder, J. T., Heidecker, G. & Rapp, U. R. *Genes Dev.* 6, 545–556 (1992)) respectively as templates. The 5' terminus was constructed to insert in frame with the GAL4 (1–147) sequences at the EcoR1 site; the pMA424 Sal1 site was used for the 3' terminus of the raf sequences. The reading frame and the $C_{168} \rightarrow S$ mutation were verified by DNA sequencing. The V12GrasH and the rap1b sequences inserted into pACTII were generated using PCR, and inserted in frame with the GAL4 transactivation domain II sequences using the BamH1 and Xho1 sites. The ΔCT constructs lacked the DNA sequences encoding the carboxyterminal 4 amino acids of Ras and Rap1b. The rap1b DNA sequences were isolated by PCR using a murine T cell cDNA library. The yeast strain GGY1::171 was transformed with the pMA424 and pACTII vector constructs according to (Ausubel, F. M. et al. in *Current Protocols in Molecular Biology*, Chapter 13, (Wiley Interscience, New York, 1990)) modified by addition of 10% DMSO to the transformation mixture prior to heat shock. Transformants were grown on SDHis⁻Leu⁻ plates as in (Durfee, T. et al. *Genes Develop.* 7, 555–569 (1993); Chien C. T., Bartel P. L., Sternglanz, R., Fields, S., *Proc. Natl. Acad. Sci. U.S.A.* 88, 9578–9582 (1991)) for 3 days before replica plating to X-gal containing plates, which in turn were scored for blue colonies 72 hours later.

Ras effector domain mutants which impair the interaction between V12GrasHΔCT and Raf(1–257) were analyzed as follows. As described above, the variant ras sequences were obtained by the PCR using the cognate sequence encoded in pMV7 (Marshall, M. S. et al. *Molec. Cell Biol.* 11, 3999–4004 (1991); Marshall, M. S. & Hettich, C. A. *Oncogene* 8, 425–431 (1993)) as template. Each pACTII-ras construct was verified by DNA sequencing. The vector pMA424 encoding Raf(1–257) was cotransformed into yeast with the pACTII vector without an insert, containing V12GrasHΔCT, or containing ras constructs containing mutations introduced into the V12GrasHΔCT background: $D_{45} \rightarrow E$, $D_{38} \rightarrow N$, Δ34, $D_{38} \rightarrow A$, $N_{26}H_{27} \rightarrow GI$, and $D_{30}E_{31} \rightarrow EK$. After 3 days growth on selective media, the colonies were replica plated to selective media containing X-gal and scored for blue colonies 3 days later. Cotransformations of the same set of pACTII V12GrasHΔCT variants with pMA424 Raf(1–257, $C_{168} \rightarrow S$) were done in parallel. No blue colonies were detected when those transformants were grown on X-gal plates.

In table 1, the β-galactosidase activity of the selected clones described above is quantified and this activity compared to the known transforming activity and p120 Ras-GAP and NF1 binding of the Ras mutants. Analysis of Ras effector domain mutations on Ras-Raf interaction in yeast and Ras transformation potency in NIH 3T3 cells was carried out as follows. pMA424 encoding Raf(1–257) was cotransformed into yeast with the pACTII encoded V12GrasHΔCT variants. After 3 days growth on selective media, the plates were scraped and an aliquot of each pool was grown in liquid selective media to an $OD_{600}$ of 0.8. A whole cell suspension was permeabilized and assayed in triplicate for β-galactosidase activity using o-nitrophenyl β-D-galactoside (Ausubel, F. M. et al. in *Current Protocols in Molecular Biology*, Chapter 13, (Wiley Interscience, New York, 1990)). The data on transformation efficiencies in NIH 3T3 cells and relative binding to NF1/GAP are taken from (Marshall, M. S. & Hettich, C. A. *Oncogene* 8, 425–431 (1993)); the transformation data are for full-length V12GrasH polypeptides, whereas the NF1/GAP binding refers to c-ras polypeptides.

The data in Table 1 indicate that there is a strong correlation between the ability of these Ras effector domain mutants to transform NIH 3T3 cells and their ability to activate lacZ expression by interacting with the Raf aminoterminal regulatory domain.

Ras-Raf complex

These findings demonstrate that Raf and Ras can bind to each other directly, as measured in vitro using purified polypeptides and in situ using a yeast expression system dependent on physical reconstitution of GAL4 DNA binding and transactivating domains. The Raf domain that participates in Ras binding is the Raf aminoterminal regulatory region, and the integrity of the Raf cysteine finger, a structure known to be crucial for the interaction of Raf with upstream-activating elements, is likewise crucial for its direct binding with Ras, in vitro and in situ. An intact effector domain of Ras is necessary for interaction with Raf, and mutations in and around the Ras effector domain impair Ras-transforming activity in parallel to the impairment in the ability of Ras to interact with Raf in situ (Table I). The binding of Raf(1–257) to c-rasH does not alter the rate of Ras GTPase, but inhibits the stimulation of Ras GTPase activity by Ras-GAP, consistent with competitive binding of both the Raf and GAP polypeptides to the Ras effector domain. The Ras carboxyterminal domain, including the S-farnesyl moiety, does not appear crucial for Ras-Raf interaction. Rap-1b also interacts strongly with the Raf aminoterminal domain, providing a plausible mechanism for antagonism between Ras and Rap-1a/b, through the generation of a nonproductive Rap-1/Raf complex, as occurs with Rap-1a and Ras-GAP (Quillam, L. A. et al. *Molec. Cell Biol.* 10, 2901–2908 (1990)).

In view of the considerable evidence that identifies Raf as an indispensable downstream effector of the mitogenic response to Ras, the present data show that the Raf-1 kinase is a direct target of the active Ras polypeptide. The Ras-Raf interaction described herein probably reflects the first step in the Ras-mediated activation of Raf-1 kinase in situ.

Screening assays

The invention can also be used to screen a candidate compound for the ability to inhibit the interaction of Ras with Raf.

In one screening method, the two-hybrid expression system described above can be used to screen for compounds capable of inhibiting Ras-Raf interaction in vivo. In this system, a GAL4 binding site, linked to a reporter gene such as lacZ, is contacted in the presence and absence of a candidate compound with a GAL4 binding domain linked to a Raf fragment and a GAL4 transactivation domain II linked to a Ras fragment. Expression of the reporter gene is monitored and a decrease in said expression is an indication that the candidate compound inhibits the interaction of Ras with Raf.

In another screening method, candidate compounds can be evaluated for anti-proliferative activity by contacting Raf or a Ras-binding fragment of Raf with a candidate compound and determining binding of the candidate compound to the peptide. Raf or Ras-binding fragment of Raf can be immobilized using methods known in the art such as binding a GST-Raf fusion protein to a polymeric bead containing glutathione. Binding of the compound to the Raf polypeptide is correlated with the ability of the compound to disrupt the signal transduction pathway and thus inhibit cell proliferation.

Candidate compounds can be screened for the ability to bind to Ras or a Raf-binding fragment of Ras. Similarly, compounds can be screened as above for the ability to bind to Raf or a Rap-binding fragment of Raf to identify a compound with anti-proliferative activity.

In another screening method, one of the components of the Ras-Raf binding complex, such as Ras or a Raf-binding fragment of Ras or Raf or a Ras-binding fragment of Raf, is immobilized. Polypeptides can be immobilized using methods known in the art, such as adsorption onto a plastic microtiter plate or specific binding of a GST-fusion protein to a polymeric bead containing glutathione. For example, GST-Raf(1–257) can be bound to glutathione-Sepharose beads. The immobilized peptide is then contacted with the labeled peptide to which it binds (Ras in this case) in the presence and absence of a candidate compound. Unbound peptide can then be removed and the complex solubilized and analyzed to determine the amount of bound labeled peptide. A decrease in binding is an indication that the candidate compound inhibits the interaction of Ras with Raf.

The invention is not limited to screening for compounds which bind to Ras residues 1–186, Ras residues 32–40, Raf residues 1–257 or Raf residues 152–168. One skilled in the art can identify the appropriate Ras or Rap binding fragments of Raf for screening candidate inhibitory or binding compounds by selecting Raf fragments which are capable of binding to Ras or Rap. Similarly, fragments of Ras to be used in screening assays can be identified by their ability to bind to Raf.

A variation of the above-described screening method can be used to screen for another class of candidate compounds which are capable of disrupting a previously-formed Ras-Raf interaction. In this example, a complex comprising Ras or a Raf-binding fragment thereof bound to Raf or a Ras-binding fragment thereof is immobilized as described above and contacted with a candidate compound. The dissolution of the complex by the candidate compound correlates with the ability of the candidate compound to disrupt or inhibit the interaction of Ras with Raf.

Antibodies

Antibodies to Ras-binding peptides of Raf, Raf-binding peptides of Ras, and the Ras-Raf complex are also useful. Specific antibodies which bind to the binding domains of Ras and Raf can be used to inhibit the interaction between the two polypeptides and their interaction with other ligands. Antibodies which bind to the complex can be also be used therapeutically to inhibit interactions of the complex in the signal transduction pathway leading to cell proliferation. Such antibodies can also be used diagnostically to measure abnormal expression of Ras or Raf, or the aberrant formation of the complex, which may be indicative of a disease state. These antibodies may also be used to study oncogenesis or to study receptor and non-receptor signal transduction pathways.

Peptides of the invention and the Ras-Raf complex can be used as antigens to immunize animals for the production of polyclonal antisera using standard protocols.

Antibodies directed against specific antigens may be detected by any of several methods known to those skilled in the art, e.g., by using an Ouchterlony double diffusion assay or an enzyme-linked immunoabsorbent assay (ELISA). In double diffusion assays, antigen and antibodies are placed in separate wells cut in a matrix, e.g., agarose on the surface of a glass plate. The contents of both wells diffuse through the matrix in all directions. Where the diffusing antigen and antigen-specific antibodies meet, a precipitin line forms. ELISA involves coating a substrate, e.g., well in a plastic dish, with a purified antigen. Serum to be tested is then added to the well. If present, antigen specific antibodies attach to the antigen coating the well. Non-binding material is washed away and a marker enzyme e.g., horse radish peroxidase or alkaline phosphatase, coupled to a second antibody directed against the antigen-specific primary antibody is added in excess and the non-adherent material is washed away. Finally the enzyme substrate is added to the well and the enzyme catalyzed conversion is monitored as indicative of presence of the antigen.

To produce monoclonal antibodies, antibody-producing cells from the challenged animal can be immortalized (e.g. by fusion with an immortalizing fusion partner) to produce monoclonal antibodies. Monoclonal antibody-producing hybridomas can then be screened for antibody binding as described above.

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or a chimeric antibody, for example, an antibody which contains the binding specificity of a murine antibody, but in which the remaining portions are of human origin.

USE

Peptide therapy

The methods of the invention are useful in treating diseases characterized by unwanted proliferation of cells. The invention provides methods of inhibiting the Ras-Raf interaction by administering peptides or peptide fragments.

Peptides may be administered to the patient intravenously in a pharmaceutically acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

Since blocking the association of Ras with Raf interferes with receptor-mediated activation of immune cells, this method may also be useful in downregulating the immune response in patients with autoimmune diseases such as systemic lupus erythematosus (SLE), type 1 diabetes, and rheumatoid arthritis. Suppression of an immune response using this method may also be useful in the treatment of allograft or xenograft recipients to prevent rejection of a transplanted organ.

Therapeutic administration of a polypeptide intracellularly can also be accomplished using gene therapy, wherein a nucleic acid which includes a promoter operatively linked to a sequence encoding a heterologous polypeptide is used to generate high-level expression of the polypeptide in cells transfected with the nucleic acid. DNA or isolated nucleic acid encoding peptides of the invention may be introduced into cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

Pharmaceutically acceptable carriers are biologically compatible vehicles which are suitable for administration to an animal: e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule in the case of gene therapy.

OTHER EMBODIMENTS

Also within the invention are fragments and analogs of the peptides of the invention.

The term "fragment", as applied to a polypeptide, will ordinarily be at least about 10 amino acids, usually about 20 contiguous amino acids, preferably at least 40 contiguous amino acids, more preferably at least 50 contiguous amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

Analogs can differ from the native peptides of Ras or Raf by amino acid sequence, or by modifications which do not affect the sequence, or by both.

Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. Table 2 lists a number of conservative amino acid substitutions.

Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into polypeptides, are well known in the art. Similarly, the replacement of an L-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

Modification of these peptides to improve penetration of the blood-brain barrier would also be useful. Polypeptides may be altered to increase lipophilicity (e.g. by esterification to a bulky lipophilic moiety such as cholesteryl) or to supply a cleavable "targetor" moiety that enhances retention on the brain side of the barrier (Bodor et al., *Science* 1992, vol. 257, pp. 1698–1700). Alternatively, the polypeptide may be linked to an antibody specific for the transferrin receptor, in order to exploit that receptor's role in transporting iron across the blood-brain barrier (Friden et al., *Science,* 1993, vol. 259, pp. 373–377).

TABLE 1

| pACTII insert | β-Galactosidase (Units ± S.D.) | Transformation efficiency (NIH 3T3 Cells) | Relative NF1/GAP Binding |
|---|---|---|---|
| none | 0.05 ± 0.01 | — | — |
| $V_{12}$rasHΔCT | 4.43 ± 0.12 | 1.0 | 1.0 |
| $V_{12}N_{38}$rasHΔCT | 0.40 ± 0.01 | 0.01 | 0.28/0.87 |
| $V_{12}D34A_{38}$rasHΔCT | 0.11 ± 0.01 | <0.001 | <.001/<0.08 |
| $V_{12}E_{45}$rasHΔCT | nd | <0.001 | 1.3/3.0 |
| $V_{12}G_{26}I_{27}$rasHΔCT | 1.38 ± 0.03 | 0.04 | 3.91/nd |
| $V_{12}E_{30}K_{31}$rasHΔCT | | | |

TABLE 2

CONSERVATIVE AMINO ACID REPLACEMENTS

| For Amino Acid | Code | Replace With |
|---|---|---|
| Alanine | A | D—Ala, Gly, Aib, β-Ala, Acp, L—Cys, D—Cys |
| Arginine | R | D—Arg, Lys, D—Lys, homo-Arg, D-homo-Arg, Met, Ile, D—Ile, Orn, D—Orn |
| Asparagine | N | D—Asp, Asp, D—Asp, Glu, D—Glu, Gln, D—Gln |
| Aspartic Acid | D | D—Asp, D—Asn, Asn, Glu, D—Glu, Gln, D—Gln |
| Cysteine | C | D—Cys, S—Me—Cys, Met, D—Met, Thr, D—Thr |
| Glutamine | Q | D—Gln, Asn, D—Asn, Glu, D—Glu, Asp, D—Asp |
| Glutamic acid | E | D—Glu, D—Asp, Asp, Asn, D—Asn, Gln, D—Gln |
| Glycine | G | Ala, D—Ala, Pro, D—Pro, Aib, β-Ala, Acp |
| Isoleucine | I | D—Ile, Val, D—Val, AdaA, AdaG, Leu, D—Leu, Met, D—Met |
| Leucine | L | D—Leu, Val, D—Val, AdaA, AdaG, Leu, D—Leu, Met, D—Met |
| Lysine | K | D—Lys, Arg, D—Arg, homo-Arg, D-homo-Arg, Met, D—Met, Ile, D—Ile, Orn, D—Orn |
| Methionine | M | D—Met, S—Me—Cys, Ile, D—Ile, Leu, D—Leu, Val, D—Val |
| Phenylalanine | F | D—Phe, Tyr, D—Thr, L-Dopa, His, D—His, Trp, D-Trp, Trans-3,4, or 5-phenylproline, AdaA, AdaG, cis-3,4, or 5-phenylproline, Bpa, D—Bpa |
| Proline | P | D—Pro, L—I-thiazolidine-4-carboxylic acid, D-or L-1-oxazolidine-4-carboxylic acid (Kauer, U.S. Pat. (4,511,390) |
| Serine | S | D—Ser, Thr, D—Thr, allo-Thr, Met, D—Met, Met(O), D—Met(O), L—Cys, D—Cys |
| Threonine | T | D—Thr, Ser, D—Ser, allo-Thr, Met, D—Met, Met(O), D—Met(O), Val, D—Val |
| Tyrosine | Y | D—Tyr, Phe, D—Phe, L-Dopa, His, D—His |
| Valine | V | D—Val, Leu, D—Leu, Ile, D—Ile, Met, D—Met, AdaA, AdaG |

---

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 257
        ( B ) TYPE: amino acid
        ( C ) STRANDEDNESS:
        ( D ) TOPOLOGY: linear ( x i ) SEQUENCE DESCRIPTION: SEQ ID NO: 1:

```
Met  Glu  His  Ile  Gln  Gly  Ala  Trp  Lys  Thr  Ile  Ser  Asn  Gly  Phe  Gly
  1              5                        10                       15

Phe  Lys  Asp  Ala  Val  Phe  Asp  Gly  Ser  Ser  Cys  Ile  Ser  Pro  Thr  Ile
               20                        25                       30

Val  Gln  Gln  Phe  Gly  Tyr  Gln  Arg  Arg  Ala  Ser  Asp  Asp  Gly  Lys  Leu
          35                        40                       45

Thr  Asp  Pro  Ser  Lys  Thr  Ser  Asn  Thr  Ile  Arg  Val  Phe  Leu  Pro  Asn
     50                        55                       60

Lys  Gln  Arg  Thr  Val  Val  Asn  Val  Arg  Asn  Gly  Met  Ser  Leu  His  Asp
 65                       70                        75                       80

Cys  Leu  Met  Lys  Ala  Leu  Lys  Val  Arg  Gly  Leu  Gln  Pro  Glu  Cys  Cys
                    85                        90                       95

Ala  Val  Phe  Arg  Leu  Leu  His  Glu  His  Lys  Gly  Lys  Lys  Ala  Arg  Leu
               100                       105                      110

Asp  Trp  Asn  Thr  Asp  Ala  Ala  Ser  Leu  Ile  Gly  Glu  Glu  Leu  Gln  Val
               115                       120                      125

Asp  Phe  Leu  Asp  His  Val  Pro  Leu  Thr  Thr  His  Asn  Phe  Ala  Arg  Lys
```

```
                    1 3 0                         1 3 5                         1 4 0
Thr    Phe    Leu    Lys    Leu    Ala    Phe    Cys    Asp    Ile    Cys    Gln    Lys    Phe    Leu    Leu
1 4 5                                1 5 0                         1 5 5                                1 6 0

Asn    Gly    Phe    Arg    Cys    Gln    Thr    Cys    Gly    Tyr    Lys    Phe    His    Glu    His    Cys
                            1 6 5                         1 7 0                                1 7 5

Ser    Thr    Lys    Val    Pro    Thr    Met    Cys    Val    Asp    Trp    Ser    Asn    Ile    Arg    Gln
                     1 8 0                         1 8 5                                1 9 0

Leu    Leu    Leu    Phe    Pro    Asn    Ser    Thr    Ile    Gly    Asp    Ser    Gly    Val    Pro    Ala
              1 9 5                                2 0 0                         2 0 5

Leu    Pro    Ser    Leu    Thr    Met    Arg    Arg    Met    Arg    Glu    Ser    Val    Ser    Arg    Met
       2 1 0                                2 1 5                                2 2 0

Pro    Val    Ser    Ser    Gln    His    Arg    Tyr    Ser    Thr    Pro    His    Ala    Phe    Thr    Phe
2 2 5                                       2 3 0                         2 3 5                                2 4 0

Asn    Thr    Ser    Ser    Pro    Ser    Ser    Glu    Gly    Ser    Leu    Ser    Gln    Arg    Gln    Arg
                            2 4 5                                2 5 0                                2 5 5

Ser
```

( 2 ) INFORMATION FOR SEQ ID NO: 2:

( i ) SEQUENCE CHARACTERISTICS:
        ( A ) LENGTH: 17
        ( B ) TYPE: amino acid
        ( C ) STRANDEDNESS:
        ( D ) TOPOLOGY: linear ( x i ) SEQUENCE DESCRIPTION: SEQ ID NO: 2:

```
Cys    Asp    Ile    Cys    Gln    Lys    Phe    Leu    Leu    Asn    Gly    Phe    Arg    Cys    Gln    Thr
1                           5                                10                                1 5

Cys
```

( 2 ) INFORMATION FOR SEQ ID NO: 3:

( i ) SEQUENCE CHARACTERISTICS:
        ( A ) LENGTH: 186
        ( B ) TYPE: amino acid
        ( C ) STRANDEDNESS:
        ( D ) TOPOLOGY: linear ( x i ) SEQUENCE DESCRIPTION: SEQ ID NO: 3:

```
Met    Thr    Glu    Tyr    Lys    Leu    Val    Val    Val    Gly    Ala    Gly    Gly    Val    Gly    Lys
1                           5                                1 0                               1 5

Ser    Ala    Leu    Thr    Ile    Gln    Leu    Ile    Gln    Asn    His    Phe    Val    Asp    Glu    Tyr
                     2 0                         2 5                                3 0

Asp    Pro    Thr    Ile    Glu    Asp    Ser    Tyr    Arg    Lys    Gln    Val    Val    Ile    Asp    Gly
              3 5                                4 0                                4 5

Glu    Thr    Cys    Leu    Leu    Asp    Ile    Leu    Asp    Thr    Ala    Gly    Gln    Glu    Glu    tyr
       5 0                                5 5                                6 0

Ser    Ala    Met    Arg    Asp    Gln    Tyr    Met    Arg    Thr    Gly    Glu    Gly    Phe    Leu    Cys
6 5                         7 0                                7 5                                       8 0

Val    Phe    Ala    Ile    Asn    Asn    Thr    Lys    Ser    Phe    Glu    Asp    Ile    His    Gln    Tyr
                            8 5                         9 0                                9 5

Arg    Glu    Gln    Ile    Lys    Arg    Val    Lys    Asp    Ser    Asp    Asp    Val    Pro    Met    Val
                     1 0 0                        1 0 5                               1 1 0

Leu    Val    Gly    Asn    Lys    Cys    Asp    Leu    Ala    Ala    Arg    Thr    Val    Glu    Ser    Arg
              1 1 5                               1 2 0                        1 2 5

Gln    Ala    Gln    Asp    Leu    Ala    Arg    Ser    Tyr    Gly    Ile    Pro    Tyr    Ile    Glu    Thr
       1 3 0                               1 3 5                        1 4 0

Ser    Ala    Lys    Thr    Arg    Gln    Gly    Val    Glu    Asp    Ala    Phe    Tyr    Thr    Leu    Val
```

```
                          145                             150                             155                             160
Arg  Glu  Ile  Arg  Gln  His  Lys  Leu  Arg  Lys  Leu  Asn  Pro  Pro  Asp  Glu
                    165                             170                             175

Ser  Gly  Pro  Gly  Cys  Met  Ser  Cys  Lys  Cys
                    180                       185
```

( 2 ) INFORMATION FOR SEQ ID NO: 4:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( x i ) SEQUENCE DESCRIPTION: SEQ ID NO: 4:

```
Tyr  Asp  Pro  Thr  Ile  Glu  Asp  Ser  Tyr
 1                        5
```

( 2 ) INFORMATION FOR SEQ ID NO: 5:

( i ) SEQUENCE CHARACTERISTICS:
        ( A ) LENGTH: 17
        ( B ) TYPE: amino acid
        ( C ) STRANDEDNESS:
        ( D ) TOPOLOGY: linear ( x i ) SEQUENCE DESCRIPTION: SEQ ID NO: 5:

```
Cys  Xaa  Xaa  Cys  Xaa  Xaa  Xaa  Xaa  Xaa  Xaa  Xaa  Xaa  Xaa  Cys  Xaa  Xaa
 1                   5                             10                        15
Cys
```

Other embodiments are within the following claims.

We claim:

1. A method of evaluating a compound for the ability to inhibit direct binding of Ras or a Raf-binding fragment thereof to Raf or a Ras-binding fragment thereof comprising:

contacting said compound with said Raf or a Ras-binding fragment thereof and said Ras or a Raf-binding fragment thereof and determining the ability of said compound to interfere with the direct binding of said Ras or a Raf-binding fragment thereof with said Raf or a Ras-binding fragment thereof, wherein a decrease in said binding in the presence of said compound compared to said binding in the absence of said compound indicates that said compound inhibits direct binding of said Ras or a Raf-binding fragment thereof to said Raf or a Ras-binding fragment thereof.

2. A method of screening a candidate compound for the ability to inhibit binding of Raf or a Ras-binding fragment thereof to Ras or a Raf-binding fragment thereof comprising:

(a) providing GAL4 binding site linked to a reporter gene;

(b) providing a GAL4 binding domain linked to either (i) said Raf or a Ras-binding fragment thereof or (ii) said Ras or a Raf-binding fragment thereof;

(c) providing GAL4 transactivation domain II linked to said Ras or a Raf-binding fragment thereof if said GAL4 binding domain is linked to said Raf or a Ras-binding fragment thereof or linked to said Raf or a Ras-binding fragment thereof if said GAL4 binding domain is linked to said Ras or a Raf-binding fragment thereof;

(d) administering said candidate compound; and (e) monitoring expression of said reporter gene, wherein a decrease in expression is an indication that said candidate compound inhibits direct binding of said Ras or a Raf-binding fragment thereof to said Raf or a Ras-binding fragment thereof.

\* \* \* \* \*